US00PP37492P2

(12) United States Plant Patent
Bacon et al.

(10) Patent No.: US PP37,492 P2
(45) Date of Patent: Jun. 30, 2026

(54) GRAPEVINE PLANT NAMED 'SUGRA78'

(50) Latin Name: *Vitis vinifera*
Varietal Denomination: SUGRA78

(71) Applicant: Sun World International, LLC, Wasco, CA (US)

(72) Inventors: Terry A. Bacon, Maplewood, NJ (US); Terrence J. Frett, Bakersfield, CA (US)

(73) Assignee: Sun World International, LLC, Wasco, CA (US)

( * ) Notice: Subject to any disclaimer, the term of this patent is extended or adjusted under 35 U.S.C. 154(b) by 0 days.

(21) Appl. No.: 19/316,883

(22) Filed: Sep. 2, 2025

(51) Int. Cl.
*A01H 5/08* (2018.01)
*A01H 6/88* (2018.01)

(52) U.S. Cl.
USPC ..... Plt./205
CPC ..... *A01H 6/88* (2018.05); *A01H 5/08* (2013.01)

(58) Field of Classification Search
USPC ..... Plt./205
CPC ..... A01H 5/08; A01H 5/00; A01H 6/88
See application file for complete search history.

(56) References Cited

U.S. PATENT DOCUMENTS

PP20,252 P3 * 9/2009 Sheehan ..... A01H 6/88 Plt./205

* cited by examiner

*Primary Examiner* — June Hwu
(74) *Attorney, Agent, or Firm* — Knobbe, Martens, Olson & Bear, LLP

(57) ABSTRACT

The new variety of grapevine 'SUGRA78' is characterized by the production of a large-sized, red and obtuse ovate berry with a mid-season ripening date. The berries of 'SUGRA78' are very firm and very juicy.

1 Drawing Sheet

Latin name of the genus and species claimed: *Vitis vinifera.*

Variety denomination: 'SUGRA78'.

BACKGROUND AND SUMMARY

This application relates to the discovery and asexual propagation of a new and distinct variety of grapevine 'SUGRA78', as herein described and illustrated. The new variety was first selected as breeder number 'GR1067R' by Terry A. Bacon and Terrence J. Frett in Wasco, Kern County, California in July 2021. The variety was originated by controlled hybridization.

The new variety 'SUGRA78' is characterized by the production of a large-sized, red and obtuse ovate berry with a mid-season ripening date. The berries of 'SUGRA78' are very firm and very juicy.

The seed parent is 'GR379B' (unpatented) and the pollen parent is 'Sugrafortyeight' (U.S. Plant Pat. No. 27,791). The parent varieties were first crossed in April 2018. The date of first sowing was March 2019, and the date of first flowering was April 2020.

The new variety 'SUGRA78' was first asexually propagated in December 2021 in Wasco, Kern County, California, by Terry A. Bacon and Terrence J. Frett using hardwood cuttings.

The new variety 'SUGRA78' can be distinguished from its pollen parent 'Sugrafortyeight' (U.S. Plant Pat. No. 27,791) in that while both varieties have rudimentary seed traces, the ripening of the berries of the new variety 'SUGRA78' starts on August $8^{th}$, compared to August $5^{th}$ for 'Sugrafortyeight'. Additionally, the new variety 'SUGRA78' has a berry weight of 9.2 g and a cluster weight of 730 g, compared to a berry weight of 11.8 g and cluster weight of 870 g for 'Sugrafortyeight'. Further, the new variety 'SUGRA78' has an obtuse ovate shaped red colored berry, compared to a black colored and broad elliptic shaped berry for 'Sugrafortyeight'

The new variety 'SUGRA78' can be distinguished from its seed parent 'GR379B' (unpatented) in that while both varieties have rudimentary seed traces and obtuse ovate shaped berry, the new variety 'SUGRA78' has a berry weight of 9.2 g and a red colored berry, compared to a berry weight of 7 g and a black colored berry for 'GR379B'. Additionally, the new variety 'SUGRA78' has a cluster weight of 730 g, compared to 650 g for 'GR379B'. Further, the ripening of the berries of the new variety 'SUGRA78' starts on August $8^{th}$, compared to August $5^{th}$ for 'GR379B'.

The fruit of the new variety 'SUGRA78' has rudimentary seed traces and a red colored berry like 'Sheegene-12' (U.S. Plant Pat. No. 20,252), but the new variety 'SUGRA78' has an obtuse ovate shaped berry, compared to an ovate shape for the berry of 'Sheegene-12'. Additionally, the new variety 'SUGRA71' has a berry weight of 9.2 g and a cluster weight of 730 g, compared to a berry weight of 8 g and a cluster weight of 600 g for 'Sheegene-12'. Further, the ripening of the berries of the new variety 'SUGRA78' starts on August $8^{th}$, compared to August $5^{th}$ for 'Sheegene-12'.

The fruit of the new variety 'SUGRA78' has rudimentary seed traces and a red colored berry like 'IFG-68-175' (U.S. Plant Pat. No. 21,664), but the new variety 'SUGRA78' has a berry weight of 9.2 g and cluster weight of 730 g, compared to a berry weight of 7.5 g and a cluster weight of 650 g for 'IFG-68-175'. Additionally, the new variety 'SUGRA71' has an obtuse ovate shaped berry, compared to the broad elliptic shaped berry of 'IFG-68-175'. Further, the ripening of the berries of the new variety 'SUGRA78' starts on August 8$^{th}$, compared to August 10$^{th}$ for 'IFG-68-175'.

The fruit of the new variety 'SUGRA78' has rudimentary seed traces and a red colored berry like 'Flame Seedless' (unpatented), but the new variety 'SUGRA78' has a berry weight of 9.2 g and cluster weight of 730 g, compared to a berry weight of 4.8 g and cluster weight of 550 g for 'Flame Seedless'. Additionally, the new variety 'SUGRA78' has an obtuse ovate shaped berry, compared to a globose shaped berry for 'Flame Seedless'. Further, the ripening of the berries of the new variety 'SUGRA78' starts on August 8$^{th}$, compared to July 5$^{th}$ for 'Flame Seedless'.

The new variety 'SUGRA78' has been shown to maintain its distinguishing characteristics through successive asexual propagations by, for example, cuttings and grafting.

Variations of the usual magnitude from the characteristics described herein may occur with changes in any of a variety of factors such as growing conditions, irrigation, fertilization, pruning, management and climatic variation.

BRIEF DESCRIPTION OF THE DRAWING

The accompanying color photographic illustration taken from a 3-year-old plant shows typical specimens of the foliage and fruit of the new grape variety 'SUGRA78'. The illustration shows the upper and lower surfaces of the leaves and exterior and sectional views of the fruit. The photographic illustration was taken shortly after the fruit was picked and the colors are as nearly true as is reasonably possible in a color representation of this type.

DETAILED DESCRIPTION

Throughout this specification, color names beginning with a small letter signify that the name of that color, as used in common speech, is aptly descriptive. Color names beginning with a capital letter designate values based upon The R.H.S. Colour Chart, published by The Royal Horticultural Society, London, England, sixth edition, 2019 reprint.

Many of the descriptive values in this specification are based on and conform to those set forth by the International Board for Plant Genetic Resources Institute Grape Descriptors (*Vitis* spp.) of 1983 and/or 1997, which was developed in collaboration with the Office International de la Vigne et du Vin (OIV) and the International Union for the Protection of New Varieties of Plants (UPOV).

The descriptive matter which follows pertains to three-year-old 'SUGRA78' plants grown in the vicinity of Wasco, Kern County, California during 2024, and is believed to apply to plants of the variety grown under similar conditions of soil and climate elsewhere.

VINE

General: (Measurements taken on three-year-old plant).

- *Vine size*.—Large. Height: Approximately 2.0 m. Width: Approximately 2.5 m.
- *Density of foliage*.—Dense.
- *Productivity*.—Very productive.
- *Crop load*.—Approximately 30 kg per vine after thinning.
- *Own root*.—Yes.
- *Training method*.—Typically cane pruned leaving about 6 canes.
- *Resistance*.—Neither resistance nor susceptibility to particular diseases or pests has been observed in this variety.

Trunk:

- *Shape*.—Stocky.
- *Diameter*.—Approximately 5 cm (at 30 cm above the soil line).
- *Straps*.—Long.
- *Inner and Outer bark color*.—Inner bark about Brownish Orange 164A and Moderate Orange Yellow 164B, weathering to about Greyish Yellow Green 196A in the outer bark.

SHOOTS

Young shoot:

- *Form of tip*.—Wide open.
- *Intensity of anthocyanin coloration of tip*.—Absent or very weak.
- *Density of prostrate hairs on tip*.—Sparse.
- *Density of erect hairs on tip*.—Absent or very weak.
- *Color*.—About Moderate Yellow Green 143D.
- *Vigor during flowering*.—Strong.

Woody shoot (observations made in the middle third of shoot):

- *Attitude before tying*.—Semi-drooping.
- *Growth of axillary shoots*.—Weak, about 7 cm in length.
- *Internode length*.—Very short, approximately 42 mm.
- *Width at node*.—Approximately 7 mm.
- *Cross section*.—Circular.
- *Lenticels*.—Absent.
- *Surface texture*.—Striated.
- *Main color*.—About Medium Greyed-Orange 175B.
- *Color of dorsal side of internode*.—About Dark Reddish Orange 175B.
- *Color of ventral side of internode*.—About Dark Reddish Orange 175B.
- *Color of dorsal side of node*.—About Dark Reddish Orange 175C and Dark Reddish Orange 175B.
- *Color of ventral side of node*.—About Dark Reddish Orange 175C and Dark Reddish Orange 175B.
- *Density of erect hairs on nodes*.—Absent.
- *Density of erect hairs on internodes*.—Absent or Very Sparse.
- *Density of prostrate hairs on internodes*.—Absent or Very Sparse.
- *Density of prostrate hairs on nodes*.—Absent or Very Sparse.

Tendrils:

- *Distribution on the shoot at full flowering*.—Discontinuous.
- *Thickness*.—Approximately 2 mm.
- *Color*.—About Strong Yellow Green 144B in midsummer.
- *Form*.—Bifurcated.
- *Number of consecutive tendrils*.—About 2.
- *Length of tendril*.—Long, approximately 20 cm.

LEAVES

Young leaves:

- *Color of upper surface of first* 4 *distal unfolded leaves*.—About Strong Yellow Green 144A.
- *Color of lower surface of first* 4 *distal unfolded leaves*.—About Strong Yellow Green 144A, Strong Yellow Green 144B, Strong Yellow Green 143A to Strong Yellow Green 143C.

*Average intensity of anthocyanin coloration of six distal leaves prior to flowering.*—Absent or very sparse.

*Density of prostrate hairs between veins at lower surface of 4th distal unfolded leaf.*—Absent or very sparse.

*Density of erect hairs between veins at lower surface of 4th distal unfolded leaf.*—Absent or very sparse.

*Density of prostrate hairs on veins at lower surface of 4th distal unfolded leaf.*—Absent or very sparse.

*Density of erect hairs on veins at lower surface of 4th distal unfolded leaf.*—Absent or very sparse.

Mature leaves (observations made on leaves in the middle third of shoot):

*Size.*—Medium.

*Average length.*—Approximately 13 cm without petiole.

*Average width.*—Approximately 16 cm.

*Shape of blade.*—Pentagonal.

*Number of lobes.*—Approximately 5.

*Mature leaf profile.*—Undulate.

*Blistering surface of blade upper surface.*—Absent or very weak.

*Goffering of blade.*—Absent or very weak.

*Leaf blade tip.*—In the plane of the leaf.

*Undulation of margin.*—Slightly undulating.

*Undulation of blade between main and lateral veins.*—Overall.

*Thickness.*—Average-typical of *Vitis vinifera* species.

*Overall shape of teeth.*—Mixture of both sides straight and both sides convex.

*Length of teeth.*—Medium, ranging from about 1 mm to 10 mm.

*Ratio length/width of teeth.*—Very small, nearly 1:1.

*General shape of petiole sinus lobes.*—Half open.

*Shape of base of petiole sinus.*—V-shaped.

*Tooth at petiole sinus.*—Absent.

*Petiole sinus limited by veins.*—Absent.

*Shape of upper leaf sinuses.*—U-shaped.

*Shape of upper lateral sinus lobes.*—Slightly overlapping.

*Depth of upper lateral sinuses.*—Shallow, approximately 3 cm to 4 cm.

*Density of prostrate hairs between veins on lower surface of blade.*—Absent to very sparse.

*Density of erect hairs between veins on lower surface of blade.*—Absent to very sparse.

*Density of prostrate hairs on main veins on lower surface of blade.*—Absent to very sparse.

*Density of erect hairs on main veins on lower surface of blade.*—Absent to very sparse.

*Density of prostrate hairs on main veins on upper surface of blade.*—Absent to very sparse.

*Autumn coloration of leaves.*—Usually about Dark Yellowish Green 139A becoming about Light Yellowish Brown 199C.

Upper leaf surface:

*Color.*—About Dark Green 135A and Dark Yellowish Green 136B.

*Surface texture.*—Smooth.

*Surface appearance.*—Dull.

*Upper surface anthocyanin coloration of main veins.*—Absent or very low.

Lower leaf surface:

*Color.*—About Moderate Yellowish Green 139B and Moderate Yellowish Green 136C.

*Surface texture.*—Smooth.

*Surface appearance.*—Dull.

*Anthocyanin coloration of main veins.*—Absent or very low.

Petiole:

*Length of petiole.*—Approximately 13 cm.

*Diameter.*—Approximately 3 mm.

*Length of petiole compared to middle vein.*—Slightly larger; about 13 cm for the petiole compared to 11 cm for middle vein.

*Density of prostrate hairs on petiole.*—Absent.

*Density of erect hairs on petiole.*—Absent.

*Color.*—About Strong Yellow Green 143D.

Buds:

*Shape.*—Conical.

*Size.*—Medium, approximately 3 mm wide×4 mm long.

*Position.*—Slightly held out.

*Bud fruitfulness.*—Basal, mostly fruitful.

*Time of bud burst.*—Early, approximately February 26$^{th}$ for the southern San Joaquin Valley region of California.

*Anthocyanin coloration of buds.*—Weak.

FLOWERS

General:

*Flower type.*—Fully developed stamen and fully developed gynoecium.

*Position of first flowering node.*—Usually 5$^{th}$ node of current season growth.

*Number of inflorescences per shoot.*—Usually 1.

*Time of full bloom.*—Approximately April 26$^{th}$ in the southern San Joaquin Valley region of California

FRUIT

General:

*Ripening period.*—Medium, beginning about August 8$^{th}$ in the southern San Joaquin Valley region of California.

*Use.*—Fresh market.

*Storage quality.*—Commercially acceptable fruit after 6 weeks of storage. The fruit of the new variety is stored between 32° F. and 36° F. with no humidity control.

Cluster:

*Form.*—Cylindrical.

*Cluster size (peduncle excluded).*—Large.

*Cluster length (peduncle excluded).*—Approximately 30 cm.

*Cluster width.*—Approximately 21 cm.

*Cluster weight.*—Approximately 730 g.

*Cluster density.*—Medium (loose-full).

*Number of berries.*—Approximately 80 berries after tipping.

Peduncle:

*Length.*—Medium, approximately 3 cm.

*Diameter.*—Approximately 10 mm.

*Lignification of peduncle.*—Weak.

*Color.*—About Strong Yellow Green 143A.

Berry:

*Size.*—Large, approximately 9.2 g.

*Dimensions*.—Width: Approximately 24 mm. Length: Approximately 34 mm.
*Uniformity of size*.—Somewhat uniform.
*Shape*.—Obtuse ovate.
*Cross section*.—Circular.
*Skin color* (*without bloom*).—About Strong Purplish Red 72A, Dark Purplish Red N79C and Moderate Reddish Purple N79D
*Flesh color*.—About Moderate Yellow Green N138C.
*Anthocyanin color of flesh*.—Absent or very weak.
*Bloom* (*cuticular wax*).—Medium, typical of most commercial *Vitis vinifera*.
*Pedicel length*.—Approximately 15 mm.
*Pedicel thickness*.—Thick, approximately 2.6 mm.
*Berry separation from pedicel*.—Moderately easy.
*Seed traces*.—Rudimentary.
*Berry firmness*.—Very firm.
*Flesh juiciness*.—Very juicy.
*Flesh texture*.—Firm and crunchy.
*Particular flavor*.—Fruity and muscat.
*Refractometer test*.—About 20 Brix.
*Titratable acidity*.—About 0.42%.
*Brix:acid ratio*.—Approximately 47.6.

Skin:
*Skin thickness*.—Medium, about 175 μm.
*Skin texture*.—Smooth.
*Skin reticulation*.—Absent.
*Skin tenacity*.—Tenacious to flesh.
*Skin tendency to crack*.—Rare.
*Skin sensitivity to sunburn*.—None.

What is claimed is:

1. A new and distinct variety of grapevine plant named 'SUGRA78' as illustrated and described herein.

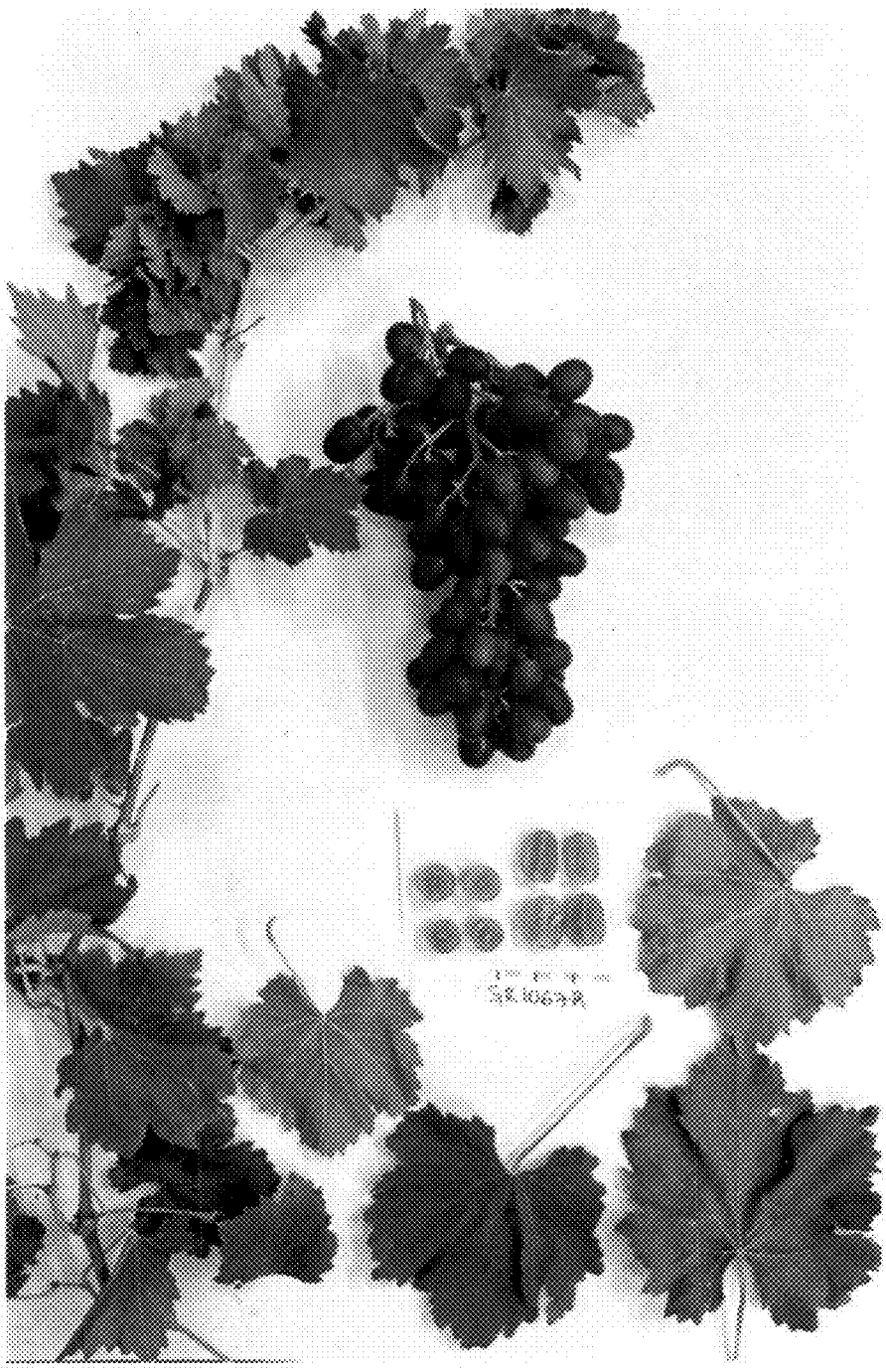

* * * * *